United States Patent [19]

Cezana et al.

[11] Patent Number: 5,192,292
[45] Date of Patent: Mar. 9, 1993

[54] SURGICAL APPARATUS USEABLE FOR ARTHROSCOPIC SURGERY

[75] Inventors: Haim Cezana, South San Francisco; Donald C. Savage, San Jose, both of Calif.

[73] Assignee: Stryker Corporation, Kalamazoo, Mich.

[21] Appl. No.: 609,156

[22] Filed: Nov. 2, 1990

[51] Int. Cl.$^5$ .............................................. A61B 17/32
[52] U.S. Cl. .................................. 606/170; 606/180; 604/22
[58] Field of Search ............... 606/79, 80, 170, 171, 606/179, 180; 604/22

[56] References Cited

U.S. PATENT DOCUMENTS

| | | | |
|---|---|---|---|
| 3,678,934 | 7/1972 | Warfield et al. | 606/79 |
| 4,014,342 | 3/1977 | Staub et al. | 606/170 |
| 4,517,977 | 5/1985 | Frost | 604/22 |
| 4,649,919 | 3/1987 | Thimsen et al. | 606/80 |
| 4,842,578 | 6/1989 | Johnson et al. | 604/22 |
| 4,986,825 | 1/1991 | Bays et al. | 604/22 |

OTHER PUBLICATIONS

Storz brochure entitled "Precision Arthroplasty System", No. SPA-1170 (4 panels).
Storz brochure entitled "Meet the Lightweight Heavyweight Arthro-Ease", No. 487-10 (4 panels).
Storz brochure entitled "The Large Joint and Microarthroplasty System . . . " (2 panels-with attached 2-panel price list).
Storz brochure entitle "We Know the Importance of Staying Sharp-", No. 1188-2500-A115 (2 panels).
Baxter brochure entitled "The PowerCut TM Surgical System", No. 104–01 88-Ortho (3 panels).
Dyonics brochure entitled "Dyonics Disposable Blades are the Right Tools", No. P/N 1060112 (3 panels).
Concept brochure entitled "Intra-Arc® Drive System", No. 812388 (4 panels).
Zimmer brochure entitled "Big on Performance", No. 97-3000-324 (4 panels).

Primary Examiner—Michael H. Thaler
Attorney, Agent, or Firm—Flynn, Thiel, Boutell & Tanis

[57] ABSTRACT

A surgical apparatus particularly useable for arthroscopic surgery includes a tool insertable in a hollow, powered handpiece. The tool includes a hollow housing in which a driven member is rotatably sleeved, which driven member is provided at its forward end with a material working portion of suitable surgical type. The tool housing and driven member adjacent their rear ends both include funnel-shaped portions adapted to receive corresponding pin-like elements on the handpiece for respectively angularly fixing the tool housing and rotatably driving the driven member.

10 Claims, 3 Drawing Sheets

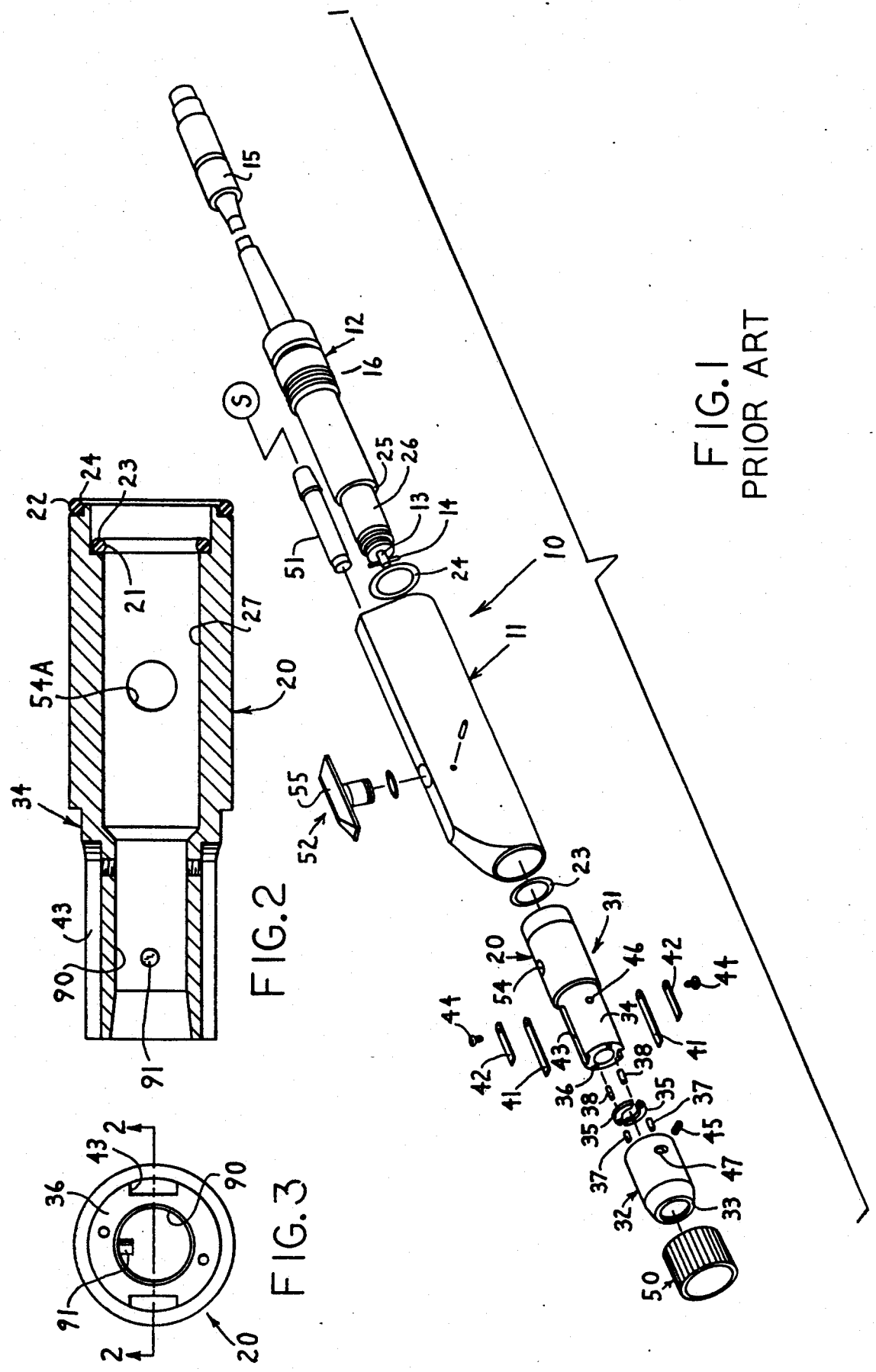

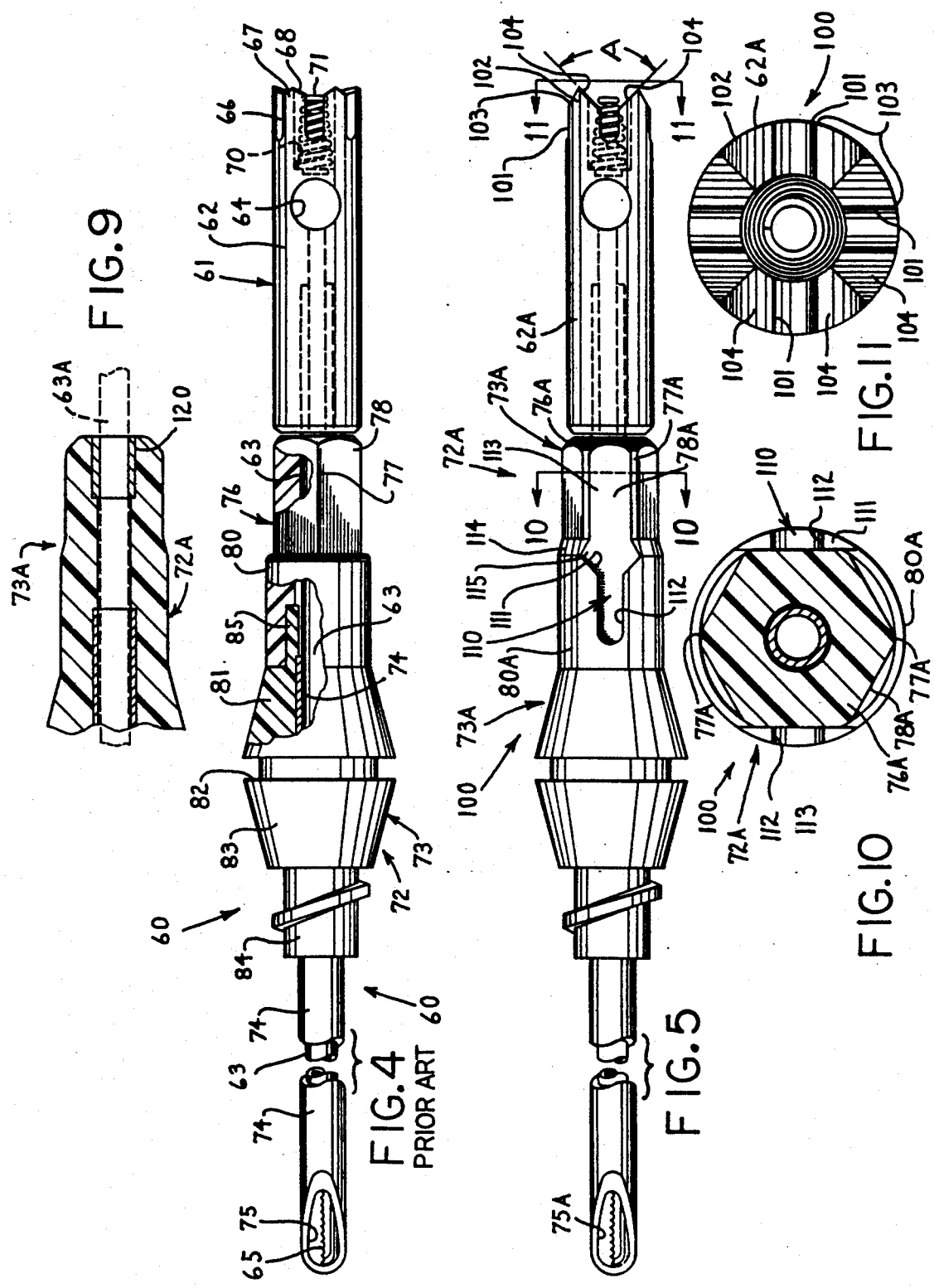

5,192,292

SURGICAL APPARATUS USEABLE FOR ARTHROSCOPIC SURGERY

FIELD OF THE INVENTION

The invention relates to a particularly useable for arthroscopic surgery and including a tool insertable in a hollow, powered handpiece, the tool being of the type having a hollow tool housing internally receiving a driven member, the forward ends of the hollow tool housing and driven member cooperating to perform a surgical procedure.

BACKGROUND OF THE INVENTION

Known tools for arthroscopic surgery include the type in which a powered handpiece is actuable to rotatably drive a tool chucked therein. One type of arthroscopic tool comprises a hollow housing to be fixedly chucked in a handpiece and having a driven member rotatably supported therein. The driven member has a rear end portion engaged and rotatably driven by a motor in the handpiece. In one such apparatus marketed by the Assignee of the present invention, the handpiece was provided with a chuck having a six-sided (hexagonal cross section) collet body for receiving a corresponding six-sided tool housing in any one of six alternatively selectable angular positions. In addition, the rear end portion of the inner, driven member of the tool was provided with six rear opening notches circumferentially spaced by six rear extending fingers. The fingers were provided with blunt rear ends angled at about 30° or less to the radial plane of the tool. The purpose was to assist guiding a diametral drive pin of the drive motor in the handpiece into a diametrally opposed pair of the rear opening notches, during loading of the tool into the handpiece. By this structure, it was intended that tools be readily loaded into and unloaded from a handpiece, to facilitate changing of tools, i.e., from one type tool to another, during the course of a surgical procedure.

However, Applicant has found under the adverse conditions sometimes found in surgery (for example, the need to focus on the surgical procedure itself rather than on loading tools in a handpiece, and the presence of irrigation and patient body liquids on tools and handpiece which may render either or both slippery), that personnel may occasionally find that insertion of a surgical tool into its handpiece is not as quick and easy as expected.

Accordingly, it is an object of the present invention to provide an improved tool and handpiece of the aforementioned type which provides for smoother and easier loading of a tool into the handpiece even under the most adverse conditions encountered during difficult surgical procedures.

It is a further object of the present invention to provide a new tool which will fit in a corresponding new handpiece, and will also fit in the prior handpiece marketed by the Assignee of the present invention with greater ease than the prior tool.

It is a further object of the invention to provide an improved tool and handpiece without significant increase in cost over the prior tool and handpiece and wherein the improved tool loads into either the prior or the new handpiece in the same manner (as a result of the same operator actions) as did the old tool into the old handpiece, and in which surgical personnel familiar with the old tool and handpiece can readily load the improved tool into either handpiece without further training or instruction.

Further objects and purposes of the invention will be apparent to those persons familiar with apparatus of this general type upon reading the following specification and inspecting the accompanying drawings.

SUMMARY OF THE INVENTION

A surgical apparatus particularly useable for arthroscopic surgery includes a tool insertable in a hollow, powered handpiece. The tool includes a hollow housing in which a driven member is rotatably sleeved, which driven member is provided at its forward end with a material working portion of suitable surgical type. The tool housing and driven member adjacent their rear ends both include funnel-shaped portions adapted to receive corresponding pin-like elements on the handpiece for respectively angularly fixing the tool housing and rotatably driving the driven member.

BRIEF DESCRIPTION OF THE DRAWINGS

FIG. 1 is an exploded pictorial view of a hand-piece useable in connection with the present invention.

FIG. 2 is an enlarged central cross-sectional view of the collet body of FIG. 1.

FIG. 3 is a left end view of the collet body of FIG. 2.

FIG. 4 is a fragmentary elevational view of a prior art tool usable with a handpiece 10 of FIG. 1.

FIG. 5 is a view similar to FIG. 4 but of a tool embodying the present invention.

FIG. 9 is a fragmentary central cross-sectional view of the rear end of the base of the tool housing of FIG. 5 showing the sleeve bearing therein.

FIG. 10 is an enlarged sectional view substantially taken on the line 10—10 of FIG. 5.

FIG. 11 is an enlarged rear view, substantially taken on the line 11—11 of FIG. 5 and looking at the rear end of the driven member of FIG. 5.

DETAILED DESCRIPTION

Figure 8C:
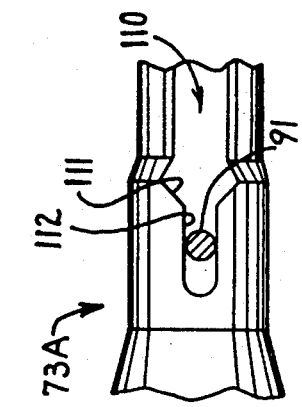
FIGS. 8A-C are fragmentary elevational views showing a sequence of positions of the base of the tool housing of the FIG. 5 tool with respect to the locator pin of the collet body of FIG. 1.

FIG. 1 discloses a powered handpiece 10 compatible with the present invention. The handpiece 10 comprises a handpiece housing 11 which is hollow from end to end for receiving fixedly therein a rotate motor 12. The rotate motor 12 is inserted through the rear (rightward in FIG. 1) end of the handpiece housing 11 and is fixed, here by threads 16, therein. The motor 12 has a forward extending shaft 13 on which is diametrally fixed a transverse drive pin 14. The motor 12 is connectable at its rear end to a connector 15 in turn connectable to a suitable power source, such as an electric power source, not shown. Actuation of the motor 12 results in rotation of the transverse drive pin 14 for driving a tool as hereafter discussed.

A hollow collet body 20 (FIGS. 1 and 2) is insertable rearwardly into the handpiece housing 11. The rear end portion of the collet body 20 has internal and external rearward facing steps 21 and 22 (FIG. 2) for receiving smaller and larger O-rings (FIG. 1) respectively. The O-ring 22 seals between the collet body 20 and the interior of the handpiece housing 11. The O-ring 23 is axially interposed between the rear facing collet body step 21 and a front facing step 25 intermediate the ends of the motor 12, such that the front part 26 of the motor, including the shaft 13, projects forward into the intermediate portion 27 of the collet body 20. The collet body 20 is fixed in the front portion of the handpiece, as by a press fit (FIGS. 1 and 2).

The collet body 20 is part of a hollow collet 31 (FIG. 1). Turning now in more detail to the collet 31, same is intended to receive therethrough a tool to be rotatably driven by the motor 12 and is further intended to releasably axially fix the tool in place in the handpiece housing 11. To this end, the collet 31 further includes a hollow lock collar 32. The lock collar 32 has a radially inward extending annular flange 33 at the front (left in FIG. 1) end thereof. The rear end of the lock collar 32 opens rearward and is adapted to sleeve over the reduced diameter forward end portion 34 of the collet body 20.

Diametrally opposed half rings 35 are housed in the front portion of the collet body 20 and are interposed between the front end 36 of the collet body 20 and the front radial flange 33 of the lock collar 32. One circumferential end (e.g. the counterclockwise circumferential end) of each half ring 35 is pivoted on a respective rear extending pivot pin 37. The two rear extending pivot pins 37 are fixed at their forward ends within the lock collar 32 near the front end thereof, in a manner not shown. The other circumferential end of each half ring 37 bears on a respective one of a pair of stop pins 38 fixed to and extending forward from the front end 36 of the collet body 20. Long and short flat springs 41 and 42 lay one under the other in an axial groove 43 extending along and opening forward through the front end of the front end portion 34 of the collet body 20. The rear ends of the flat springs 41 and 42 are fixed by a radial screw 44 to the front end portion 34 of the collet body 20. Two diametrally opposed sets of these elements 41-44 are provided on the collet body 20. The flats of the springs 41 and 42 substantially parallel the plane defined by the stop pins 38, such that the springs 41 are circumferentially halfway between the stop pins 38. The front ends of the springs 41 overhang the front end of the collet body 20 and bear on the respective half rings 35 to force same diametrally toward each other so that the clockwise end of each half ring bears forcibly against the length portion of a corresponding one of the forward extending stop pins 38. The half rings 35 form a tool gripping/releasing collet chuck. Thus, upon clockwise rotation of the lock collar 32, its pivot pins 37 attempt to rotate their respective half ring about the length axis of the collet body 20. However, the stop pins 38 prevent circumferential movement of the clockwise ends of the half rings 35, such that the half rings pivot diametrally away from each other. The collet 31 is thus open. Upon relaxation of the clockwise twisting force on the lock collar 32, the springs 41 and 42 push the half rings 35 diametrally toward each other, pivoting same about their pivot pins 37 back to their relaxed position, through the stop pins 38, rotates the lock collar 32 counterclockwise back to its original position. The collet 31 is thus closed. In summary, clockwise rotation of the lock collar 32 opens the collet 31 by moving the half rings 35 apart from each other and letting go of the lock collar 32 allows it to spring back counterclockwise and thereby allows the rings 35 to move back close to each other to thereby close the collet 31.

Rotation of the lock collar 32 is limited by a screw 45 received in a threaded, radially inward extending hole 46 in the side of the reduced diameter front end portion 34 of the collet body 20. The outer portion of the screw 45 extends through a circumferential extending slot 47 in the lock collar 32 to limit the extent of circumferential rotation of the lock collar 32 with respect to the collet body 20. A trim sleeve 50 slides rearward over the rear portion of the lock collar 32 to cover the screw 45 and is fixed on the lock collar to serve as a manual rotation grip.

In the embodiment shown, the powered handpiece 10 is provided with a vacuum, or suction, fitting 51 connectable to a conventional suction source S. The fitting 51 is fixed to the rear of the handpiece housing 11 above the motor connector 15 and communicates through a suction path (not shown) within the handpiece housing, through a barrel valve assembly generally indicated at 52 and thence through a radial hole 54 (FIGS. 1 and 2) in the collet body 20.

The radial hole 54 in the collet body 20 communicates through the hollow interior of the collet body with a diametral through hole, hereafter discussed, in the rotatably driven member of a tool (hereafter described), and forward through the length of the tool with a surgical site for removing flowable debris therefrom.

FIG. 4 shows a prior art tool 60 usable with the powered handpiece 10 of FIG. 1. The prior art tool 60 comprises a driven member 61 in turn comprising a drive shaft 62 from which fixedly, coaxially and forwardly extends a hollow shaft extension 63. A diametral through hole 64 intermediate the ends of the drive shaft 62 communicates forwardly (leftwardly in FIG. 4) with the interior of the hollow shaft extension 63. The forward end of the shaft extension has a material working portion, here for example a cutting edge 65, for carrying out a surgical procedure.

As more generally indicated above, when the tool 60 is chucked in the handpiece 10, the through hole 64 communicates with the suction hole 54 in the collet body 20 and hence with the suction path (not shown) in the handpiece housing 11 (including barrel valve assembly 52) and suction fitting 51. Suction is felt at the cutting edge 65, so that liquid can be drawn from the wound through the tool 60 and handpiece 10 toward the suction source.

At its rear end, the drive shaft 62 has six evenly circumferentially distributed, rearward opening notches 66 circumferentially spaced by six rear extending fingers 67. As seen in elevation, the rear ends of the fingers are bluntly tapered at about 30° to the length axis of the drive shaft 62, such taper being indicated at 68. The notches 66 and fingers 67 surround and extend rearward from a central, blind, rear facing recess 70 in the drive shaft 62, into which recess is insertable a coil compression spring 71.

The tool 60 further includes a hollow tool housing 72 having a hollow base 73 releasably fixable on the handpiece 10 and a hollow sleeve 74 extending forward (leftward in FIG. 4) from the hollow base 73. In the embodiment shown, the forward (leftward) end of the sleeve 74 has a laterally facing window 75 in which is exposed the cutting edge 65 of the driven member 61. In the particular unit shown in FIG. 4, the window 75 has cutting edges which coact with the cutting edge 65 of the driven member 61 as the latter rotates within and with respect to the sleeve 74 for providing a shearing type cutting action. However, tools 60 are known with a variety of different kinds of material working forward end structures. The rearwardmost portion 76 of the hollow base 73 is of hexagonal cross section, having six axial ridges 76 joining six flats 78, so as to provide six positive alternative circumferential positions thereof within a prior collet body similar to that at 20 in FIG. 1 having an internal hexagonal cross section (not shown) in its forward end portion 34. Extending forward from the hexagonal cross section rear portion 76 of the tool 60, the hollow base 73 in sequence comprises with a cylindrical portion 80 of somewhat enlarged diameter, a forwardly diverging frustoconical portion 81, an annular groove 82, a first forward portion 83 (here being substantially cylindrical but with a slight foward taper) and a reduced diameter forward end portion 84.

The frustoconical portion 81 is sized to spread the half rings 35 as the tool is inserted rearward into the front end of the powered handpiece 10 (FIG. 1). The groove 82 is intended to receive the half rings 35 and allow them to radially inwardly seat therein, in response to the radial inward urging of the springs 41 and 42, so as to lock the tool fixedly in place in the powered handpiece 10. The first forward portion 83 and forward end portion 84 of the hollow tool housing 72 (FIG. 4) protrude forwardly from the lock collar 32 when the tool 60 is installed in the powered handpiece 10. In the same condition, it will thus be seen that the hollow sleeve 74 thus also extends forward from the powered handpiece.

Figure 7:
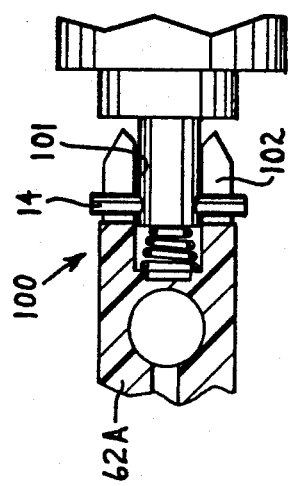
FIG. 7 is a fragmentary cross-sectional view showing the driving engagement of the parts of FIG. 6.
Figure 8B:
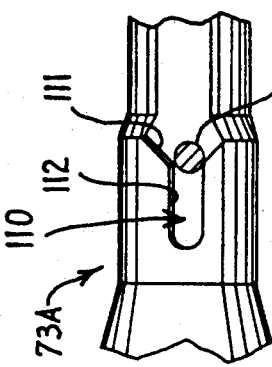
Figure 6:
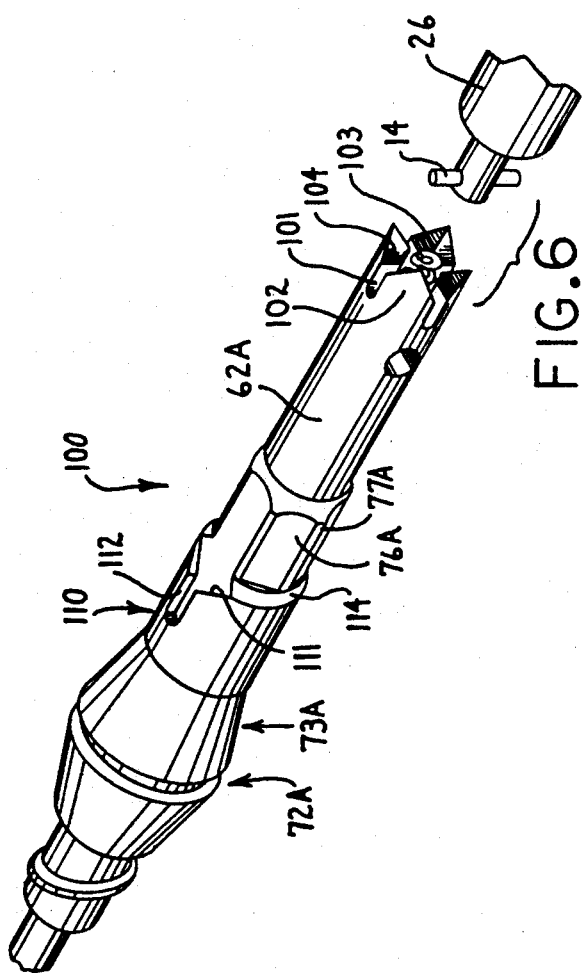
FIG. 6 is a fragmentary pictorial view of the rear end of the driven member of the FIG. 5 tool immediately prior to moving rearward into engagement with the forward extending shaft and transverse drive pin of the motor of FIG. 1.
Figure 8A:
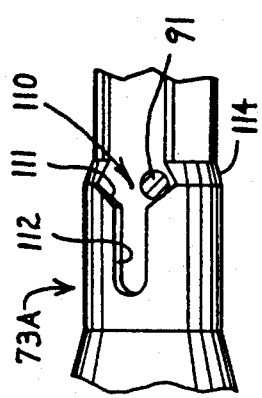

With the driven member 61 in its forward FIG. 4 position immediately adjacent the hollow tool housing 72 and with the prior tool 60 installed in a prior handpiece similar to that shown in FIG. 1, the transverse drive pin 14 (FIG. 1) of the powered handpiece is nearly fully seated (see FIG. 7) in a diametrally opposed pair of the notches 66 of the tool driven member 61, the half rings 35 of the powered handpiece are fully seated in the annular groove 82 of the hollow tool housing 72 and the front end of the tool rotatable shaft extension 63 bears, in axial thrust receiving relation, on the closed front end of the tool hollow sleeve 74.

The prior tool housing base 73 is provided in two pieces, namely a rearward piece 76,80 whose forward end sleeves over a rearward extension 85 of the forward piece 81–84. The complete forward piece 81–85 fixedly supports the rear portion of the hollow sleeve 74. In the unit shown, the rear end of the rear portion 76 serves as a radial bearing for the rotatable hollow shaft extension 63.

As stated, the structure shown in FIG. 4 is conventional. To the extent above described, the apparatus of FIGS. 1–3 is also conventional.

Turning now to apparatus more specifically embodying the present invention, the hollow interior 90 of the forward end portion 34 of the collet body 20 (FIGS. 1–3) is of circular cross section (rather than of hexagonal cross section as in the prior device above described). Further, in the present invention, a fixed locator pin 91 protrudes radially into the hollow interior 90 of the forward end portion 34 of the collet body 20.

Further, under the present invention there is provided a tool 100 (FIGS. 5–11) which differs from the prior art tool 60 as follows. Parts of the inventive tool 100, similar to the prior art tool 60, carry the same reference numerals with the suffix "A" added, for convenient reference.

In the inventive tool 100, the drive shaft 62A has at its rear end only four notches 101 (FIGS. 5, 6, 7 and 11), arranged in only two pairs of diametrally opposed notches, the two pairs being located at right angles to each other. The notches 101 are circumferentially spaced by circumferentially wider fingers 102. The rear ends of the fingers have pointed ends 103, which taper at a relatively sharp angle, here about 45°, to the length direction of the tool 100. Thus, circumferentially adjacent fingers 102 have tapered ends 103 that are opposed to each other at an included angle of about 90°, as indicated at A in FIG. 5. Such circumferentially adjacent tapered finger ends 103 have circumferentially opposed facets 104 which define respective planes which are at about a right angle to each other (the angle indicated at A in FIG. 5). Thus, each notch 101 opens rearward in a funnel-shape, as seen in profile in FIG. 5. In other words, each notch has a rear opening divergent mouth defined by such a pair of circumferentially opposed facets 104 and each notch funnel mouth defines the angle of divergence A (FIG. 5) of about 90°. Each diametrally opposed pair of notches 101 has its circumferentially opposed, rearward extending pairs of facets 104 shaped as though formed by a diametrally guided milling cutter of funnel shape. As seen from the end in FIG. 11, each facet 104 is of relatively large, substantially trapezoidal area, with an apparent end facing area approximately the same as that of the adjacent notch 101.

Surprisingly, despite its reduced number (four) of notches 101 and circumferentially wider fingers 102, the rear end of the inventive drive shaft 62A consistently and smoothly circumferentially orients itself with respect to the handpiece drive pin 14 (FIG. 6), as the inventive tool 100 is inserted rearward into the handpiece 10, so as to automatically drive the guide pin 14 fully into a given pair of diametrally aligned notches 101. There is no need for the user (surgeon or surgical assistant, for example) to try to circumferentially preorient a given diametral pair of notches 101 with the handpiece drive pin 14 before inserting the tool 100 into the handpiece 10. The prior tool 60 (FIG. 4) would occasionally balk or hesitate during insertion as the rear ends of its fingers 67 contacted the handpiece drive pin 14, and would thereby require the prior tool 60 to be eased, circumferentially shifted a bit and then pushed rearward again before a given pair of notches 66 would receive therein the handpiece drive pin 14. The inventive tool 100, with its improved drive shaft 62 has been found to eliminate this problem.

Surprisingly then, the reduced number of notch pairs and circumferentially wider fingers of the inventive tool 100 have not reduced the circumferentially self-aligning character of the drive shaft 62A, but rather have improved it over the prior drive shaft 62.

The inventive tool 100 also includes an improved tool housing 72A (FIGS. 5, 6 and 8–11), in which a pair of funnel-shaped slots 110 (FIGS. 5 and 6) are provided in the periphery of the cylindrical portion 80A of the hollow base 73A on diametrally opposite sides thereof. Each funnel-shaped slot 110 opens rearwardly and is comprised by a wide, rear opening mouth 111 which diverges rearwardly at an included angle of about 90° and with each side of the diverging mouth 111 being at about 45° to the length direction of the tool 100. The slot 110 further includes a uniform width throat 112 extending forward coaxially from the mouth 111. The front end of the throat 112 is closed by a semi-circular front end (FIG. 5). The radial depth of the slot 110 is constant throughout its axial length and is defined by a flat floor 113 which extends rearward (rightward in FIG. 5) from the funnel-shaped slot (i.e. groove) 110 to the rear end of the hollow base 73A.

The funnel-shaped slots 110 of the inventive tool 100 are each circumferentially located, in the preferred embodiment shown, so that the floor 113 thereof is coplanar with and continues rearward into a corresponding one of the six flats 78A (FIG. 5) forming the hexagonal shape of the rear portion 76A. This leaves the six ridges 77A and six flats 78A of the hexagonal cross section in place in the inventive tool 100, like in the prior tool 60.

The maximum diameter of the hollow base 73A is reduced somewhat from the cylindrical portion 80 rearward to the rear portion 76A by a sloped step 114 (FIG. 5). As seen in plan, in FIG. 5, the mouth 111 and floor 113 widen rearward to the sloped step 114. The flat floor narrows rearward at 115 through the extent of the sloped step 114, to the circumferential width of the connected flat 78A. The mouth 111 is thus circumferentially wider than each flat 78A.

Since the rear portion 76A of the hollow base 73A substantially retains the hexagonal form of the corresponding rear portion 76 of the FIG. 4 prior art tool 60, the rear portion 76A, and hence the entire inventive tool 100, is capable of insertion in a prior art handpiece of the kind above discussed with respect to FIG. 1, in which the front interior portion is hexagonally shaped to non-rotatably receive the hexagonal cross section rear end portion 76 of the prior art tool 60. Thus, the inventive tool 100 advantageously can be used with prior art handpieces in place of the prior art tool 60.

On the other hand, the new tool 100, in view of its diametrally opposed funnel-shaped slots 110 in the cylindrical portion 80A, is also insertable in the improved collet body 20 of the inventive FIG. 2,3 embodiment. More particularly, as the inventive tool 100 is inserted rearward (rightward in the drawings) through the lock collar 32 and into the hollow collet body 20, the circumferential locator pin 91 in the collet body 20 will axially encounter either the open mouth 111 of one of the two funnel-shaped slots 110 in the hollow tool housing base 73A or the sloped, rear facing step 114 which circumferentially connects the rear ends of the two mouths 111.

The two mouths 111, between them, extend more than a third of the circumference of the rear end of the hollow base 73A. Thus, in at least one third of the range of relative circumferential starting positions of the hand-piece 10 and tool 100, the locator pin 91 of the hand-piece collet body 20 will directly enter the funnel-shaped slot 110.

Otherwise, the locator pin 91 will first encounter the sloped rear facing step 114. When this occurs, the operator feels positive resistance to further insertion, i.e. feels a definite stop, whereupon the operator simply twists the exposed forward portion of the hollow tool housing 72A clockwise or counterclockwise less than about a third turn, during which time the sloped rear facing step 114 slides smoothly circumferentially along the locator pin 91. Gentle rearward pressure applied during this circumferential movement causes the locator pin 91 to enter the the funnel mouth 111 (FIG. 8A) and bear on the adjacent side of the funnel mouth 111.

This smoothly circumferentially centers the funnel-shaped slot 110 on the locator pin 91, while allowing movement of the hollow tool housing 72A rearward with respect to the locator pin 91, and indeed the entire handpiece 10, in the sequence shown in 8B and 8C. In this way, the locator pin 91 smoothly enters the throat 112 to a point near the blind front end thereof, whereupon the tool 100 is fully inserted in the handpiece 10.

In contrast, the prior tool 60 and handpiece with their hexagonal matching cross-sections above discussed, must be placed in a much narrower range of relative circumferential starting positions, much less than a third of the circumference thereof, before their hexagonal cross-sections will telescope relative to each other. This is easily seen to be true because the ribs 76 of the tool 60 will interfere with the flats within the handpiece and so must be closely aligned with the channels between flats in the handpiece, before telescoping can begin.

The radially inward extent of the locator pin 91 is limited so that it clears the ridges 77A (FIGS. 6 and 10) in the rear portion 76A of the hollow base 73A, so that the ridges 77A do not interfere with relative circumferential movement between the hollow base 73 and locator pin 91. Despite this, the locator pin 91 extends radially inward sufficient to reliably engage the edges of the funnel mouth 111.

In contrast to the two-piece (76,80 and 81-84) hollow base 73, the inventive hollow base 73A is essentially a one-piece molding, with the addition of a small sleeve bearing 120 inserted fixedly in the rear (right-ward) end thereof to rotatably support the shaft extension 63A. This one-piece construction permits the depth of the funnel-shaped slots 110 to be sufficient to reliably, positively engage the pin 91 of the handpiece without danger of breaking through the radially interior face of the cylindrical portion 80A, as would be the case with the prior art cylindrical portion 80 of FIG. 4.

As a further aspect of the present invention, it is preferred that the collet body 20 (and thus the entire collet 31) be rotated 90° clockwise (looking rightward in FIG. 1) from its prior position shown in FIG. 1, so that the pin 91 is at the top and the grooves 43 face right and left in FIG. 3. This allows insertion of the inventive tool 100 into the handpiece with its funnel-shaped slots 110 facing up and down, and hence with its cutting window 75A (FIG. 5) facing either straight up or down with the handpiece housing 11 upright as shown in FIG. 1.

To allow proper suction flow from the inventive tool 100 through the handpiece housing 11, with the collet body 20 thus rotated to its inventive FIG. 3 position, the hole 54A is compensatingly shifted 90° on the collet body, about the length axis thereof, so as to remain on top of the collet body and thus still aligned in the suction passage through the conventional housing 11.

Although a particular preferred embodiment of the invention has been disclosed in detail for illustrative purposes, it will be recognized that variations or modifications of the disclosed apparatus, including the rearrangement of parts, lie within the scope of the present invention.

The embodiments of the invention in which an exclusive property or privilege is claimed are defined as follows:

1. In surgical apparatus particularly usable for arthroscopic surgery, a tool adapted for insertion in a hollow, powered handpiece, the tool comprising:

a hollow tool housing having a hollow base insertable rearwardly into a hollow handpiece and a hollow sleeve extending forward from said base;

a driven member having a drive shaft drivable by a handpiece and a shaft extension protruding forward from said drive shaft and insertable forwardly into the rear end of said hollow tool housing to extend from said base along said sleeve;

the improvement comprising means radially indented in said base for accepting a radially inward extending locator element in the hollow handpiece, said indented means defining a groove opening radially outwardly in the periphery of said base, said groove having a mouth and a throat extending forward from said mouth, said groove having a radially outward facing floor blocking communication between the interior and exterior of said hollow base at said groove, whereby a radially inward extending handpiece locator element can enter the mouth of the groove and be guided thereby along said floor into said throat to positively angularly locate said tool housing in the handpiece, in which said base includes a noncircular, rearwardly extending, hollow tail, said tail having multiple sides, one side of which tail continues rearwardly said radially outward facing floor of said groove.

2. The tool of claim 1 in which said groove floor and said one side of said tail are coplanar flats.

3. The tool of claim 2 in which said sides of said tail are respective flats of a hexagonal cross-section, the portion of said base occupied by said groove being of diameter greater than the maximum diameter of said hexagonal cross-section, two diametrally opposed ones of said grooves being provided on said base.

4. The tool of claim 1 in which said groove and said side of said tail are of substantially constant radial depth as they extend axially along said base, said groove having a blind forward end, there being two diametrally opposed ones of said grooves on said base, said groove mouth having sides at approximately 45° to the length axis of said tool.

5. In surgical apparatus particularly usable for arthroscopic surgery, a tool adapted for insertion in a hollow, powered handpiece, the tool comprising:

a hollow tool housing having a hollow base insertable rearwardly into a hollow handpiece and a hollow sleeve extending forward from said base;

a driven member having a drive shaft drivable by a handpiece and a shaft extension protruding forward from said drive shaft and insertable forwardly into the rear end of said hollow tool housing to extend from said base along said sleeve;

the improvement comprising means radially indented in said base for accepting a radially inward extending locator element in the hollow handpiece, said indented means defining a groove opening radially outwardly in the periphery of said base, said groove having a mouth and a throat extending forward from said mouth, said groove having a radially outward facing floor blocking communication between the interior and exterior of said hollow base at said groove, whereby a radially inward extending handpiece locator element can enter the mouth of the groove and be guided thereby along said floor into said throat to positively angularly locate said tool housing in the handpiece, in which said hollow base includes a front portion and a rear portion from which said drive shaft is rearwardly extendible, said base rear portion including first means for nonrotative engagement in a desired angular position in a first handpiece, said first means including a rearwardly extending chordal flat facing radially outward of said base first portion, in which said flat continues rearwardly a central part of said funnel mouth of said groove, said base front portion being of maximum diameter greater than the maximum diameter of said base rear portion.

6. The tool of claim 5 in which the drive shaft has a rear end defined by four similar rear opening notches evenly circumferentially spaced by four similar rear extending fingers, said fingers having rear tips each tapered on both circumferential edges at approximately 45° to the axial direction of the drive shaft as seen in elevation.

7. In surgical apparatus particularly usable for arthroscopic surgery, a tool adapted for insertion in a hollow, powered handpiece, the tool comprising:

a hollow tool housing having a hollow base mountable on a handpiece and a hollow sleeve extending forward from said base;

a driven member having a drive shaft drivable by a handpiece and a shaft extension protruding forward from said drive shaft and insertable in said hollow tool housing to extend from said base along said sleeve;

the improvement comprising:

first means on said base for nonrotatably locating said base in a desired angular position in a first handpiece, said first means including radially outwardly facing noncircular surface means extending forward from the adjacent rear end of said base for fixedly angularly locating said base in a first handpiece;

second means on said base for nonrotatably locating said base in a desired angular position in a second handpiece structurally different from said first handpiece, said second means being located forward of said first means on said base, said second means including funnel-shaped groove means extending forward from said first means for fixedly angularly locating said base in a second handpiece;

such that said tool is alternatively usable in handpieces having structurally differing tool base engaging portions.

8. The tool of claim 7 in which said funnel-shaped groove opens radially outwardly and is closed radially inward by a radially outward facing floor.

9. The tool of claim 7 in which said noncircular surface means of said first means comprises the peripheral surface of a hexagonal cross-section tail, said second means comprising a substantially circular cross-section head extending forward coaxially from said tail, said peripheral surface of said hexagonal cross-section tail having circumferentially arranged flats, said groove having a floor extending rearward into a coplanar one of said flats.

10. A surgical apparatus particularly usable for arthroscopic surgery, comprising:

a powered handpiece including
a hollow collet body having a hollow central passage and a locator element protruding radially into said passage, and
motor means including a rotatable shaft communicating with said passage and having a drive element; and a tool including
- a hollow tool housing including a hollow base insertable in said passage in said collet body and having a generally funnel-shaped groove indented in the periphery thereof, said groove having radially outward facing floor and a wide rear opening mouth which converges forwardly along said floor and a uniform width throat extending along said floor forwardly from the mouth, in which said base includes a noncircular, multi-sided, rearwardly extending, hollow tail, one side of which tail continues rearwardly said radially outward facing floor of said grooves, said groove being sized to receive said locator element, such that upon rearward insertion of said tool base into said collet body passage in a relatively wide range of relative angular positions, the locator element enters the wide mouth of the groove, from said one side of said tail, and is guided by said mouth into said throat, said tool further including a driven member including a drive shaft, said drive shaft being disposed rearwardly of said hollow base of said tool and being insertable into said passage past said locator element and into contact with said drive element, so as to complete a rotatable driving connection of said motor means to the drive shaft of said tool.

* * * * *

UNITED STATES PATENT AND TRADEMARK OFFICE
CERTIFICATE OF CORRECTION

PATENT NO. : 5 192 292
DATED : March 9, 1993
INVENTOR(S) : Haim Cezana et al

It is certified that error appears in the above-identified patent and that said Letters Patent is hereby corrected as shown below:

Column 11, line 13; change "grooves" to ---groove---.

Signed and Sealed this

Seventh Day of December, 1993

Attest:

BRUCE LEHMAN

Attesting Officer

Commissioner of Patents and Trademarks